(12) United States Patent
Johnson

(10) Patent No.: US 8,734,160 B2
(45) Date of Patent: *May 27, 2014

(54) OPERATING ROOM EDUCATIONAL TELEVISION "OREDUTV"

(76) Inventor: Lanny L. Johnson, Okeemos, MI (US)

(*) Notice: Subject to any disclaimer, the term of this patent is extended or adjusted under 35 U.S.C. 154(b) by 313 days.

This patent is subject to a terminal disclaimer.

(21) Appl. No.: 12/537,942

(22) Filed: Aug. 7, 2009

(65) Prior Publication Data

US 2009/0298032 A1    Dec. 3, 2009

Related U.S. Application Data

(63) Continuation of application No. 11/744,978, filed on May 7, 2007, now Pat. No. 7,572,127, which is a continuation-in-part of application No. 11/551,862, filed on Oct. 23, 2006, now abandoned.

(51) Int. Cl.
    *G09B 7/00*    (2006.01)
(52) U.S. Cl.
    USPC ........................................................ 434/262
(58) Field of Classification Search
    USPC ........................................................ 434/262
    See application file for complete search history.

(56) References Cited

U.S. PATENT DOCUMENTS

| | | | |
|---|---|---|---|
| 5,810,601 A | 9/1998 | Williams | |
| 6,038,331 A | 3/2000 | Johnson | |
| 6,373,942 B1* | 4/2002 | Braund | 379/430 |
| 6,554,619 B2 | 4/2003 | Williams | |
| 6,606,479 B2* | 8/2003 | Cook et al. | 434/350 |
| 6,727,818 B1 | 4/2004 | Wildman et al. | |
| 6,882,278 B2 | 4/2005 | Winings et al. | |
| 7,372,367 B2 | 5/2008 | Lane et al. | |
| 7,485,115 B2* | 2/2009 | Nakamura | 434/262 |
| 2002/0044059 A1* | 4/2002 | Reeder et al. | 340/573.1 |
| 2005/0021369 A1* | 1/2005 | Cohen et al. | 705/2 |
| 2008/0020361 A1* | 1/2008 | Kron et al. | 434/262 |

* cited by examiner

*Primary Examiner* — Kathleen Mosser
(74) *Attorney, Agent, or Firm* — David J. Dawsey; Michael J. Gallagher; Gallagher & Dawsey Co., LPA

(57) ABSTRACT

An apparatus for viewing information includes a wireless interactive monitor including a screen for displaying the information and adapted to receive the information wirelessly and a surgeon scrub sink for allowing a surgeon to sterilize the hands of the surgeon, positioned under the wireless interactive monitor.

8 Claims, 5 Drawing Sheets

OPERATING ROOM EDUCATIONAL TELEVISION "OREDUTV"

CROSS-REFERENCE TO RELATED APPLICATIONS

This application is a continuation of U.S. patent application Ser. No. 11/744,978, filed on May 7, 2007, which is a continuation in part of U.S. patent application Ser. No. 11/551,862, filed on Oct. 23, 2006, now abandoned; the contents of each are herein incorporated by reference in their entirety.

FIELD OF THE INVENTION

The present invention is directed generally to an Internet based wireless or wired communication device, and more particularly, to a system and method for maintaining a video image for interactive communication at areas in the surgical suite of a hospital or clinic to transmit educational instruction of pertinent and timely information for the medical profession. In one embodiment, the device would be in the surgical suite located above the surgical scrub sinks.

BACKGROUND OF THE INVENTION

Due to recent federal legislation as well as new educational institutional policies, pharmaceutical and medical device companies are banned from providing any significant financial assistance or incentive to the doctors or the medical staff in order to promote their products or services. Traditional marketing methods included the use of company employees to entertain, gift, or otherwise incentive medical personnel to listen to or to see presentations concerning the respective company's products or services. In response to the loss of this traditional method, the medical companies have taken to marketing their products directly to the public via commercial media. i.e. television, magazines, newspapers. The thrust of such marketing is to motivate the potential patient to ask their doctor about the product. Often, this is the first notification of such a product. It is no longer the direct relationship with the supplier for information, but it is the patient who is now the agent of information. This method often is confusing to the patient who may lack medical understanding and novel to the physician or staff who was not prepared educationally to respond to the patient's inquiry. The problem now is how to get this timely educational information to the medical profession. Continuing medical education is provided by the hospitals, universities, and medical societies, but these are monthly or less frequent.

This problem is further complicated by the doctor's and staff's available time being limited. Daily patient care activities minimize or eliminate daily education opportunity. There is little time available on a daily basis to learn about the new products or services of the pharmaceutical or medical device companies for the above reasons.

Furthermore, immediately prior to or during an actual operation or treatment, there may be a need to review these new products or services in order to treat the patient or to obtain the latest information about the actual operation or treatment.

Prior to an operation, surgeons and staff spend a significant amount of total time washing his/her hands and forearms, even multiple times each day. The period of time "scrubbing" is typically three to ten minutes at a surgical scrub sink. It is a time of isolation from any and all other activities. Therefore, this is an opportune time for short segments of video and or sound bites concerning relevant medical educational material. Surgical sinks are used in order to permit a surgeon to wash his/her hands prior to entering the surgical suite and subsequent placement of the sterile surgical gloves for surgery. Furthermore, the surgical sinks are located in or near the operating room and consequently may be difficult to hard wire. It is essential, in order to maintain the sterile conditions, that the surgeon's hands not touch any object which might be unsterile. Voice or physical mode for activation is possible for selection from the menu on the television monitor for the program of their choosing; by their specialty or their academic interest.

Technology continues to enter the operating room. Presently, surgery can be aided with 3-D vision. This was a technology that was originally developed by the military to help fighter pilots immerse themselves in air combat. The same technology is helping surgeons. Surgeons set a pair of sophisticated goggles over their head to view the surgery with the aid of cameras inserted into incisions into the patient as their surgical tools are inserted below the skin. The surgeons can obtain a real-time view of the effect of their surgery. However, this does not address the need of the surgeon for instantaneous training and guidance for unexpected problems.

U.S. Pat. No. 6,369,799 discloses a method and apparatus for controlling a computer screen adapted for use by individuals with limited or no manual dexterity.

Because of the closeness of the scrub sink to the OR room, there may be a need to avoid excess noise from or in consideration of other doctors and staff members.

SUMMARY OF THE INVENTION

An object of this invention is to provide an automatically or manually operated monitor and surgical scrub sink which overcomes the above disadvantages.

A further object of this invention is to provide such a surgical scrub sink and wireless interactive monitor which can be wirelessly or wire connected to an information source which includes pharmaceutical or other types of information which would be useful for the surgeon. Consequently, while the surgeon is cleaning his hands, he can activate the wireless interactive monitor in order to obtain additional information such as pharmaceutical information. This may be accomplished by infra red transmission methods.

Wireless communications devices, such as the monitor and the cell phone, typically include a housing and various data input and output devices, such as a keyboard, a display, a microphone and a speaker. In addition, some wireless communications devices have video conferencing capabilities. The same system may be used for in-service educational training of the support staff on new procedures, medications or instrumentation.

In accordance with this invention, a wireless interactive monitor is positioned over the sink. An electronically operated on/off mechanism controls the wireless interactive monitor positioned near or approximately under the surgeon scrub sink. The wireless interactive monitor may be voice activated and controlled so that the surgeon does not need to physically touch the monitor. The interactive monitor may include a computer in order to perform the voice activation of the interactive monitor and to perform the voice control of the interactive monitor. A sensor may be mounted under or alongside the tub for directing a beam in front of the tub at the height of the user's legs so as to detect the presence and absence of a user in the immediate vicinity of the tub. The sensor is operationally connected to the on/off mechanism so as to comprise a control for turning on the monitor when the presence of the user is detected and turning off the monitor when the absence of a user is detected. The sensor provides an alternative to voice activation. The activation may be by foot pedal.

The sensor may be operative over a focal distance of approximately a few inches so as to avoid false starts by detecting objects other than the surgeon standing in the immediate vicinity of the tub. A further preferred practice of the invention provides mounting the sensor on a support arm which extends below and generally to the front edge of the tub so as to assure properly locating the short focus sensor at its desired location. The support arm may be suspended from the tub by mounting the support arm to the tub drain pipe. The support arm may be used for mounting the mixing valve for the faucet.

Implementation may involve leasing or purchasing the air space in and about the hospital and/or the operating room suite, specifically those areas of transmission; i.e. above and in front of the scrub sink, in the operating room, the instrument ready rooms, physicians and nurses' lounges. The present invention may be used in convention in hotel rooms. It can also be used in cars, planes, buses, trains etc. Bill Gates has indicated that advertising and TV as we know it today will be passe very soon. This invention furthers that notion.

An apparatus for viewing information includes a wireless interactive monitor including a screen for displaying the information and adapted to receive the said information from a memory and a surgeon scrub sink for allowing a surgeon and/or hospital personnel to sterilize the hands of the surgeon, positioned under the wireless interactive monitor. The memory receives the information wirelessly.

Additionally, the present invention includes an apparatus for viewing information including a wireless interactive monitor including a screen for displaying the information and adapted to receive the information wirelessly and a surgeon 3-D vision apparatus for allowing a surgeon to view a 3-D image. The 3-D vision apparatus is coupled to the wireless interactive monitor.

The wireless cellular phone of the present invention receives a video image provided by a video-output device of a wireless communications device, and as a result enables a surgeon of the wireless communications device to receive information in the form of video and audio through the display and the speaker and to provide feedback by the buttons to the video-output device in order to instruct the video-output device which information that the surgeon would like to see and hear.

BRIEF DESCRIPTION OF THE DRAWINGS

The invention may be understood by reference to the following description taken in conjunction with the accompanying drawings, in which, like reference numerals identify like elements, and in which.

DETAILED DESCRIPTION

The present invention involves improvements over surgical scrub sinks utilizing automatic control apparatus for turning the wireless interactive monitor on and off. Although the present invention is described in terms of a wireless device, the principles of the present invention can be equally applied to a wired system including a wired interactive monitor.

The concepts of the invention may be practiced with various types of known surgical scrub sinks wherein the invention is incorporated therein by providing a sensor mounted at a location which would generally correspond to the legs, and more particularly the knee area, at the immediate vicinity of the sink tub. Preferably, the sensor is of short focus with a focal distance of about 2-6 inches, so as to avoid false signals which would otherwise be caused by detecting objects other than the user of the sink. The invention is based upon the recognition that when the user of the sink, such as a surgeon, is performing a hand scrubbing operation, he or she will stand immediately juxtaposed to the sink tub during the scrubbing or hand washing operation and will remain in that position until the scrubbing operation is completed, although during the scrubbing operation there might be periods of time when the hands are not in the immediate vicinity of the faucet. During this period of time, the surgeon is free to view the material presented on the interactive wireless monitor. Thus, the present invention could rely upon detection of the hands near the faucet as well as the detection of the legs near the tub. The monitor 102 which may shut itself off after a predetermined amount of time or could be shut off by voice-activated command. Although the present invention is described in terms of the interactive monitor 102 positioned above a scrub sink 10, other locations within the surgical suite are within the scope of the present invention. For example, the interactive monitor 102 could be positioned to the left of or to the right of the scrub sink 10. Furthermore, the present invention describes the user of the interactive monitor 102 and a scrub sink 10 as a surgeon, but other users such as nurses and assistants could take advantage of the interactive monitor 102. The scrub sink 10 could be found in the preparation area and could be used to clean surgical instruments between cases. Individuals who are not familiar with the various instruments, their care, use, safety, and sterilization issues could use the interactive monitor 102 for tutorials which is sometimes called in-service education. The interactive monitor 102 could be positioned in a doctors or nurses lounge and might be used with earphones 404, which may be wireless or wired, that allows each person to hear their individualized program without disturbing others in the room or area.

Figure 3:
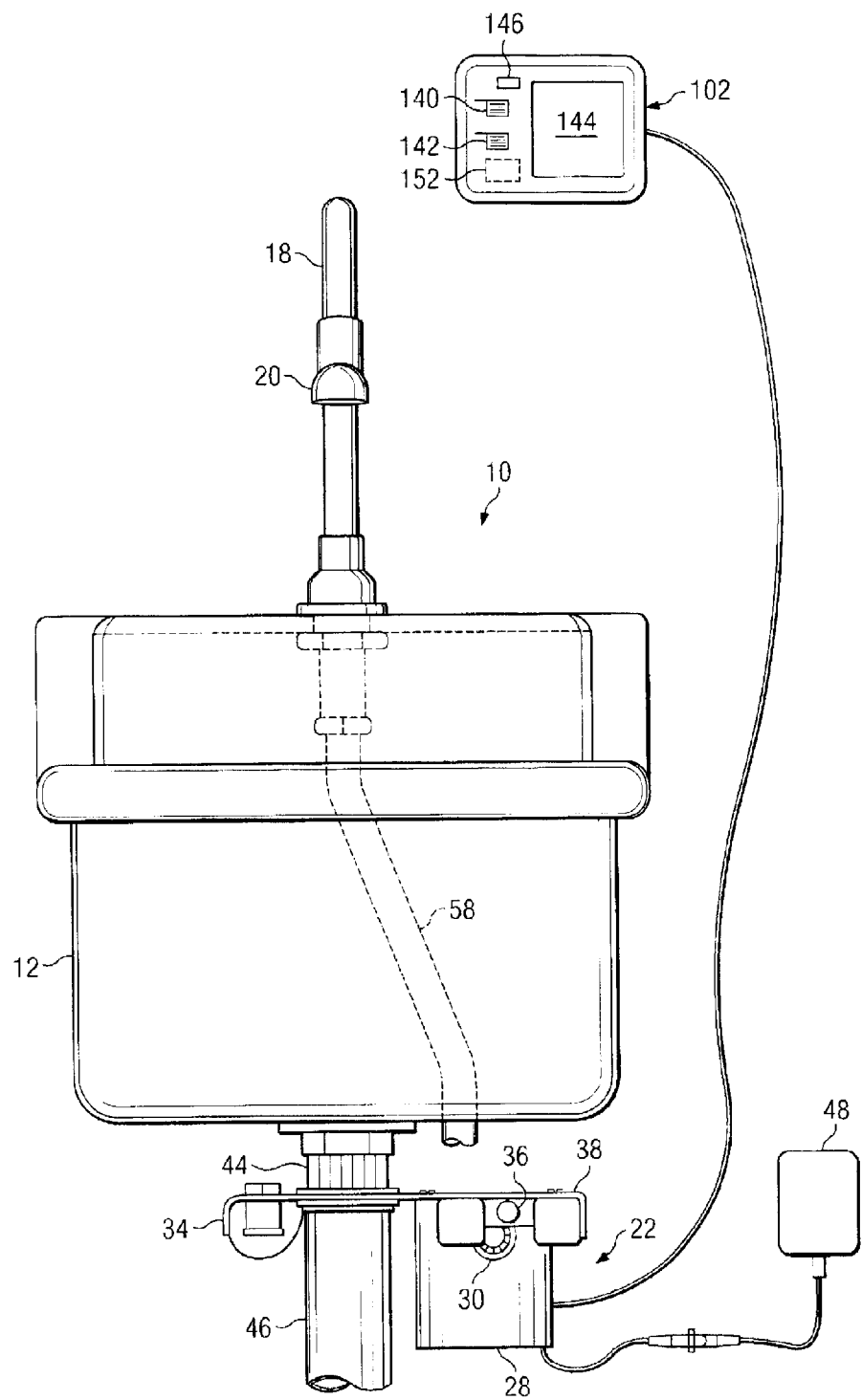
FIG. 3 illustrates a front view of the wireless interactive monitor and surgeon sink of the present invention.
Figure 4:
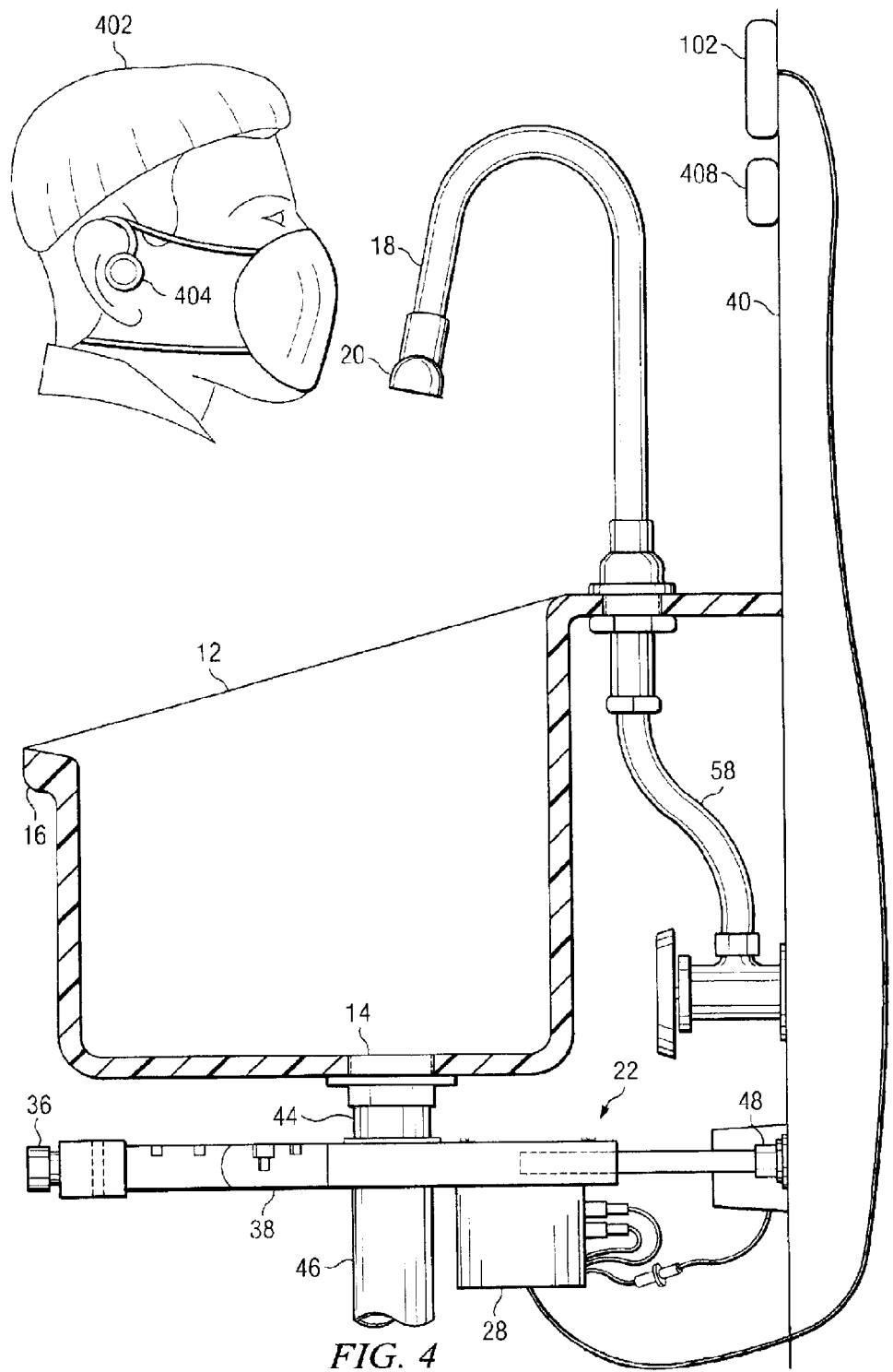
FIG. 4 illustrates a side view of the wireless interactive monitor and the surgeon sink of the present invention.

As illustrated herein and in FIGS. 3-4, a surgical scrub sink 10 is shown which includes a tub 12 of any suitable known description and wireless interactive monitor 102. The tub 12 would include a drain hole 14 at its lower portion and would include a front edge 16. A faucet 18 is mounted at the top of tub 12. The faucet 18 terminates in a nozzle 20 which is disposed over and toward the open body of tub 12.

The wireless interactive monitor 102 is electronically operated by an on/off mechanism 22 as described above, or the wireless interactive monitor 102 could be voice-activated by user 402. The user 402 may use a wired or wireless ear piece 404 which could be attached to the user 402 before the user 402 washes his hands and could be removed by an attendant to maintain the sterile condition of the hands. Such on/off mechanism 22 may include, for example, a solenoid controlled electronic switch in order to turn on and off the electric power for the wireless interactive monitor 102 in housing 28. A sensor module cable 30 is also provided in housing 28.

The housing or enclosure 28 for the on/off mechanism 22 is mounted to a support arm 34. A sensor 36 is mounted to the remote or free end of support arm 34 as best shown in FIGS. 3-4. Support arm 34 includes a main bracket 38 which is fixedly mounted to any suitable support. For example, as best illustrated in FIG. 3, the main bracket 38 is attached to drain tube 44 of tub 12 and is stabilized against rotation by a pair of wall adjustment screws bearing against wall 40. Tub 12 is secured directly to wall 40.

Advantageously, support arm 34 is utilized for mounting various components of the surgical scrub sink 10. As noted, sensor 36 and on/off mechanism 22 are mounted to support arm 34. Support arm 34 is suspended from tub 12 by connection to drain tube 44 leading from drain hole 14. Tube 44 is mounted to and through support arm 34 with the tail piece 46 extending downwardly below support arm 34. As illustrated in the various figures, the on/off mechanism 22 includes a transformer 48 mounted at any suitable location, such as to wall 40. The wiring for transformer 48 is electrically connected to the wiring from on/off mechanism 22. The on/off mechanism also includes a wire to connect to the wireless interactive monitor 102. Transformer 48 may be of any suitable known construction such as a 12 volt transformer.

Sensor cable 30 is housed within the downwardly extending sides of arm 34 and is connected to sensor 36. The position of sensor module 36 could be adjusted to its intended location with respect to the front edge 16 of tub 12. This assures that the module will detect the presence or absence of the user standing in front of and at or juxtaposed to front edge 16 of tub 12. Accordingly, it is possible to use a short focus sensor having an effective focal distance of about 2-6 inches and still reliably sense the presence or absence of a surgeon standing at sink 10. The elevation of sensor 36 above the floor would be selected to correspond to the elevation of the surgeon's legs, such as in the knee area. Other locations of the surgeon's legs could also be used as the detecting target. Thus, sensor module 36 could be elevated above the floor any suitable distance of, for example, six inches to thirty inches.

The invention would thus be practiced by suitably positioning sensor module 36 at the desired location, generally at the front edge 16 of tub 12. Sensor module 36 would project a beam which operates to detect the presence or absence of an object in the range of the beam. Because sensor module 36 preferably operates with a focus, the presence of an object would be detected only when the object is in the immediate vicinity of front edge 16 at the elevation of sensor module 36. Thus, under ordinary conditions, no object would be detected. This detection of the absence of an object would permit the on/off mechanism 22 to remain in its off condition and the wireless interactive monitor 102 would remain off. When, however, a surgeon steps to sink 10 in order to perform a scrubbing operation by standing at the front edge 16 of sink 10, sensor module 36 would detect the presence of an object, namely the surgeon's legs and the sensing would be transmitted to on/off mechanism 22 and permit the wireless interactive monitor 102 to be activated. The wireless interactive monitor 102 would remain on as long as the surgeon remained at the front of tub 12. Once the scrubbing operation has been completed, the surgeon would step away from tub 12. Sensor 36 would then detect the absence of the surgeon and corresponding signal would be sent to the on/off mechanism 22. The wireless interactive monitor 102 would then shut off. The monitor 102 could be controlled by the apparatus 404 described above for individuals with limited or no manual dexterity. In this case, the surgeon cannot use his/her hands because of the need for a sterile environment.

An optional manual override switch is also provided to facilitate continued operation of the wireless interactive monitor 102 should there be an interruption in power to the mechanism 22. This override switch is linked to a backup battery power pack to maintain actuation of the on/off mechanism 22, and resultant operation of the wireless interactive monitor 102 in case of a power failure.

The invention thus provides a way of automatically controlling the wireless interactive monitor 102 during scrubbing which permits full movement of the surgeon's arms and hands during the scrubbing without affecting the operation of the wireless interactive monitor 102. The wireless interactive monitor 102 shuts off once the video is completed and the surgeon is no longer present at sink 10.

The wireless interactive monitor 102 of the present invention receives a video image provided by a video-output device 104 of a wireless communications device, and as a result enables a surgeon of the wireless communications device to receive information in the form of video and audio and to provide feedback to the video-output device 104 in order to instruct the video-output device 104 which information that the surgeon would like to see and hear. The feedback would allow the surgeon to take appropriate action to maintain or adjust the content of the video image. The present invention may be readily implemented in any wireless communication device. The principles of the present invention are applicable to any wireless communication device, including, but not limited to, analog and digital cellular telephones, personal communications system (PCS) devices, and the like.

Figure 7:
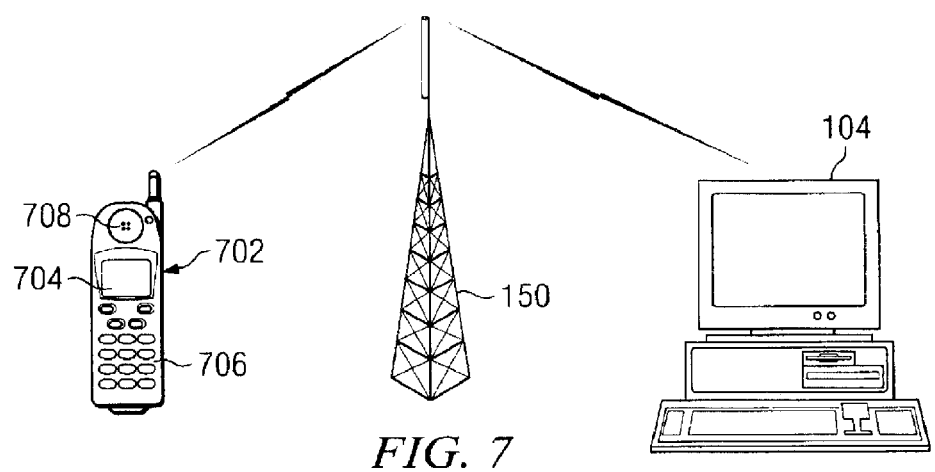
FIG. 7 illustrates a cell phone being used in accordance with the teachings of the present invention.

The wireless cellular phone 702 as shown in FIG. 7 of the present invention receives a video image provided by a video-output device 104 of a wireless communications device, and as a result enables a surgeon of the wireless communications device to receive information in the form of video and audio through the display 704 and the speaker 708 and to provide feedback by the buttons 706 to the video-output device 104 in order to instruct the video-output device 104 which information that the surgeon would like to see and hear. The feedback would allow the surgeon to take appropriate action to maintain or adjust the content of the video image. The present invention may be readily implemented in any wireless communication device.

Figure 1:
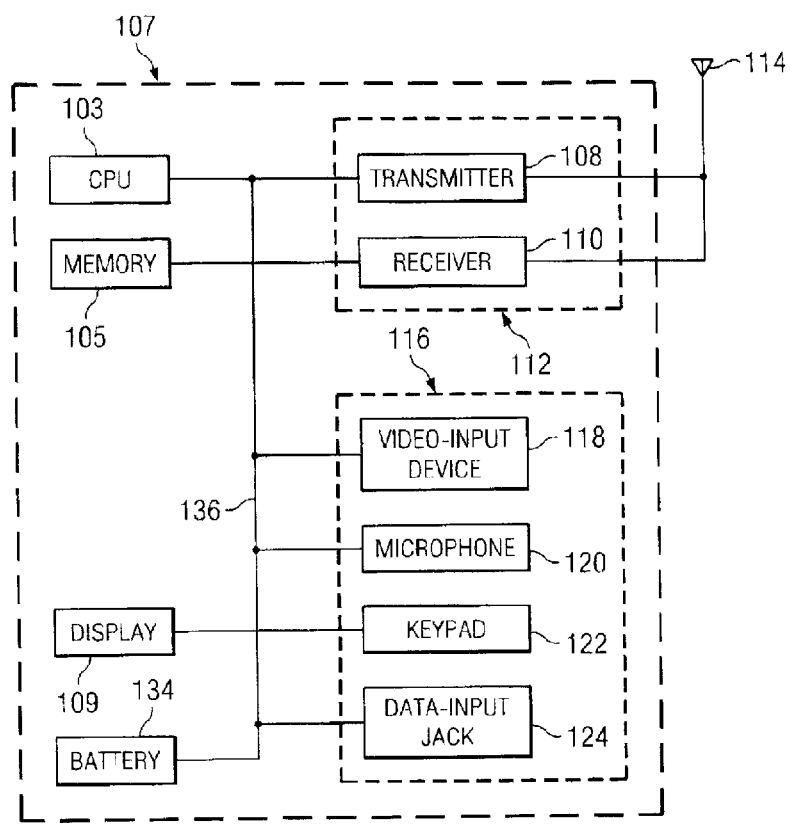
FIG. 1 illustrates a computer diagram of the video output device of the present invention.

The present invention is embodied in a system 100 illustrated in the functional block of FIG. 1. The system 100 includes a central processing unit (CPU) 103, which controls operation of the system. A memory 105, which may include both read-only memory (ROM) and random-access memories (RAM), provides instructions and data to the CPU 103. A portion of the memory 105 may also include non-volatile random-access memory. The display 109 provides a screen for CPU 103.

Figure 2:
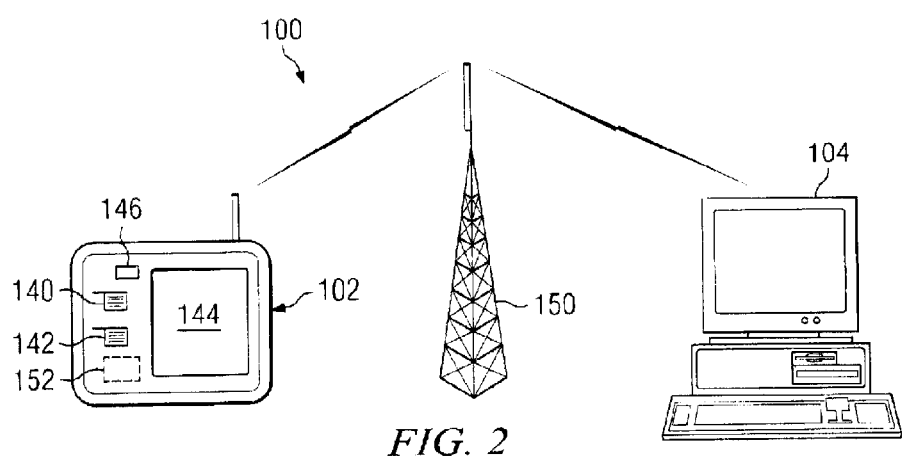
FIG. 2 illustrates the video output device and the wireless interactive monitor of the present invention.

The system 100, which is typically embodied in a wireless communication device, also includes a housing 107 that contains a transmitter 108 and a receiver 110 to allow transmission and reception of data, such as audio and video communications and programming data, between the system 100 and a remote location, such as the monitor 102 or the like. The transmitter 108 and the receiver 110 may be combined into a transceiver 112. The transmitter 108 and receiver 110 may be connected to transmit and receive wireless Internet. An antenna 114 is attached to the housing 107 and electrically coupled to the transceiver 112. Although FIG. 1 illustrates the antenna 114 as extending from the housing 107, some designs may include an internal antenna that is contained completely within the housing. FIG. 2 illustrates a tower 150 which may be located at the hospital or some other convenient location to connect the wireless signal to the video output device 104. The wireless signal may be a wireless Internet signal.

A user-input device 116 includes a video-input device 118, is communicatively linked to the system 100 for operation by the user in a conventional manner. The user-input device 116 provides a convenient way which audio, commands, video images, voice data and other data may be entered by the user. Although FIG. 1 illustrates the user-input device 116 as including a video-input device 118 to input video for example from the medical companies to be ultimately displayed on the monitor 102, a microphone 120, a keypad 122, and a data-input jack 124 for example to connect to the Internet so that video and other data can be obtained and contained within the housing 107, other user input devices may be used, such as the receiver, and the like, and in various combinations. In addition, while the video-input device 118 may be a camera, DVD, CD, or tape, video-input devices 118 may be used, including the data-input jack 124, the receiver 110, and the like, and in various combinations.

Electrical components of the system 100 receive power from a battery 134, which is attached to and supported by the housing 107. In an exemplary embodiment, the battery 134 is a rechargeable battery. In other embodiments, the system 100 may include a connector (not shown) for the connection of an external power source, such as an automobile power adapter, AC power adapter, or the like.

The various components of the system 100 are coupled together by a bus system 136 which may include a power bus, control bus, and status signal bus in addition to a data bus. For the sake of clarity, however, the various buses are illustrated in FIG. 1 as the bus system 136.

FIG. 3 illustrates the operation of the system 100 to transmit the video image and audio to a remote location, such as the wireless interactive monitor 102. The video image and audio may be transmitted to a variety of remote locations, such as another system 100, or the like. For the sake of brevity, the system 100 will be described using a limited number of examples.

In operation, the sensor 36 senses the presence of the surgeon at the surgical scrub sink 10 and activates the on/off mechanism 22 to its on condition. The content that is presented to the user on the monitor 102 may be customized. For example a first surgeon may desire to see only information relating to his specialty such as brain surgery. A second surgeon may specialize in plastic surgery and is only interested in information that relates to plastic surgery. The CPU 503 could recognize the earpiece 404 as being dedicated to a particular surgeon or the earpiece 404 could include a keyboard to input a unique identifier. Alternatively, a keypad 408 could be positioned near the monitor 102 to identify the user. The CPU 503 would direct appropriate video and/or audio to the monitor 102 based upon the user that is currently using the system. This sensor may be individualized for the surgeon so that the medical or surgical specialties of interest to him/her would be pre-programmed. The on/off mechanism 22 activates the wireless interactive monitor 102. Alternatively, the monitor 102 may go in and out of the suspended, sleep or hibernate mode. Initially, a first menu 140 and a second menu 142 appear on the screen 144 of the wireless interactive monitor 102 which may be a screen for a computer monitor or a screen for a television set. The surgeon may start the wireless interactive monitor 102 by a voice command using the speech recognition technology 152. The surgeon chooses either the first menu 140 or the second menu 142 by either physically activating the screen of the wireless interactive monitor 102 at the appropriate first menu 140 or the second menu 142 or using speech recognition technology 152 of the monitor 102, the surgeon speaks his choice for the first menu 140 or the second menu 142 which is received by the voice-recognition technology 152 to activate the first menu 140 choice or the second menu 142 choice. Either the first menu 140 choice or the second menu 142 choice is wirelessly sent to the video-output device 104 as feedback. The feedback is received by the antenna 114 and transmitted to the receiver 110 which transmits the feedback to the CPU 103. The CPU 103 uses the feedback to select audio and video, only audio or only video from the memory 105. Using audio and video as an example, the CPU 103 directs the audio and video to the transmitter 108, and the transmitter 108 transmits the audio and video to the antenna 114 which in turn is wirelessly transmitted to the wireless interactive monitor 102 to be received and played on the screen of the wireless interactive monitor 102. This continues until the audio or video transmitted from the transmitter 108 ends or the surgeon walks away from the surgical scrub sink 10 at which point the sensor 36 fails to detect the surgeon standing in front of the surgical scrub sink 10. The sensor 36 directs the on/off mechanism 22 to turn off the wireless interactive monitor 102, and the on/off mechanism 22 turns off the wireless interactive monitor 102. A voice command could be used to turn off the wireless interactive monitor 102 by utilizing the speech recognition technology 152.

Alternatively, instead of watching the video over the Internet, the videos may be downloaded from the Internet or directly input into a user input 516 and saved in a memory 505. Consequently, when a new video is made available by the pharmaceutical company, the new video can be instantly downloaded into the memory 505. The monitor 102 may include additional processing circuitry 500 including a central processing unit (CPU) 503, which controls operation of the processing circuitry 500, a memory 505, which may include both read-only memory (ROM) and random-access memories (RAM), provides instructions and data to the CPU 503 and may provide for the storage of video which has been downloaded from the Internet or input through the user input device 516. A portion of the memory 505 may also include non-volatile random-access memory. The monitor 102 provides a screen for CPU 503.

Figure 5:
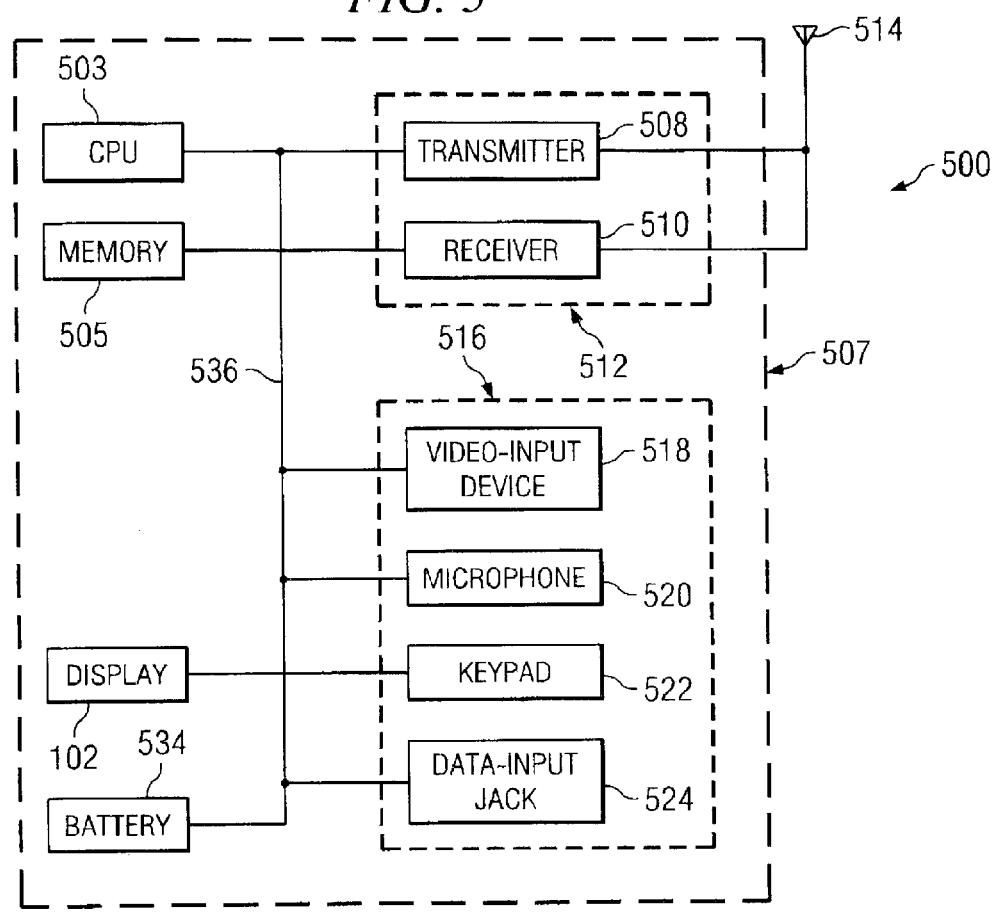
FIG. 5 illustrates a computer diagram associated with the monitor of the present invention.

The system 100, which is typically embodied in a wireless communication device, also includes a housing 507 that contains a transmitter 508 and a receiver 510 to allow transmission and reception of data, such as audio and video communications and programming data, between the video output device 104 and the monitor 102 or the like. The transmitter 508 and the receiver 510 may be combined into a transceiver 512. The transmitter 508 and receiver 510 may be connected to transmit and receive wireless Internet. An antenna 514 is attached to the housing 507 and electrically coupled to the transceiver 512. Although FIG. 5 illustrates the antenna 514 as extending from the housing 507, some designs may include an internal antenna that is contained completely within the housing 507.

A user-input device 516, comprising at least a video-input device 518, is communicatively linked to the CPU 503 for operation by the user in a conventional manner. The user-input device 516 provides a convenient way which audio, commands, video images, voice data and other data may be entered by the user of the monitor 102. Although FIG. 5 illustrates the user-input device 516 as comprising a video-input device 518 to input video for example from the medical companies to be stored in memory 505 and ultimately displayed on the monitor 102, a microphone 520, a keypad 522, and a data-input jack 524 for example to connect to the Internet so that video and other data can be obtained and contained within the housing 507, other user input devices may be used, such as the receiver, and the like, and in various combinations. In addition, while the video-input device 518 may be a camera or tape, video-input devices 518 may be used, including the data-input jack 524, the receiver 510, and the like, and in various combinations.

Electrical components of the monitor 102 receive power from a battery 534, which is attached to and supported by the housing 507. In an exemplary embodiment, the battery 534 is a rechargeable battery. In other embodiments, the system 100 may include a connector (not shown) for the connection of an external power source, such as an automobile power adapter, AC power adapter, or the like.

The various components of the monitor 102 are coupled together by a bus system 536 which may include a power bus, control bus, and status signal bus in addition to a data bus. For the sake of clarity, however, the various buses are illustrated in FIG. 5 as the bus system 536.

In operation, the sensor 36 senses the presence of the surgeon at the surgical scrub sink 10 and activates the on/off mechanism 22 to its on condition. The on/off mechanism 22 activates the wireless interactive monitor 102. Initially, the first menu 140 and the second menu 142 appear on the screen 144 of the wireless interactive monitor 102 which may be a screen for a computer monitor or a screen for a television set. The surgeon may start the wireless interactive monitor 102 by a voice command using the speech recognition technology 152. The surgeon chooses either the first menu 140 or the second menu 142 by either touching the screen of the wireless interactive monitor 102 at the appropriate first menu 140 or the second menu 142 or using speech recognition technology 152 of the monitor 102, the surgeon speaks his choice for the first menu 140 or the second menu 142 which is received by the voice-recognition technology 152 to activate the first menu 140 choice or the second menu 142 choice. Either the first menu 140 choice or the second menu 142 choice is wirelessly sent to the CPU 503 as feedback. The CPU 503 directs the memory 505 began playing the video to be displayed on the monitor 102. This will facilitate high quality, full resolution, and continuous video.

The monitor 102 could be placed in the waiting room to provide waiting room educational television. Additionally, the monitor 102 could be portable such that the monitor 102 could travel with the patient as the patient goes to the lab or x-ray. Alternatively the monitor 102 could be placed in the operating room OR so that the surgeon can obtain additional information relating to the medical problem he is currently addressing such as a solution for an unexpected problem with the patient which could replace a medical implant/instrument employee.

Figure 6:
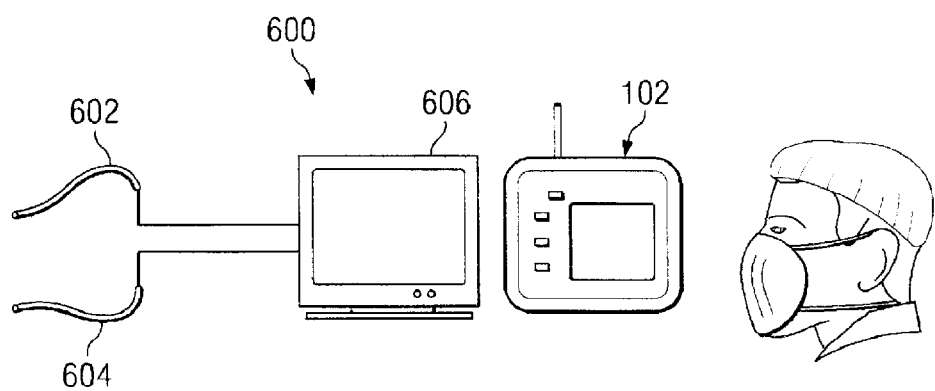
FIG. 6 illustrates a diagram of a 3-D system with the monitor of the present invention.

FIG. 6 illustrates a 3-D system 600 which includes a first video camera 602 and a second video camera 604 to be placed under the skin of the patient to view of the operation. In addition, the cameras provide a 3-D video to the display 606 and in close proximity to display 606 is the monitor 102 which is reduced in size so that the surgeon can view video from the medical companies in conjunction with the videos from the actual surgery. Implementation may involve leasing or purchasing the air space in and about the hospital and/or the operating room suite, specifically those areas of transmission; i.e. above and in front of the scrub sink, in the operating room, the instrument ready rooms, physicians and nurses' lounges. The present invention may be used in convention in hotel rooms. It can also be used in cars, planes, buses, trains etc. Bill Gates has indicated that advertising and TV as we know it today will be passe very soon. This invention furthers that notion.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed.

What is claimed is:

1. A method of providing medical instruction or information to a health care provider performing a medical procedure, comprising:
   a) providing a wireless interactive monitor comprising:
      i) a central processing unit (CPU) operably connected to memory, wherein said CPU recognizes a plurality of potential users,
      ii) a display monitor for displaying information from said CPU, and
      iii) a transmitter for wirelessly transmitting or receiving commands or information, said transmitter operably connected to said CPU;
   b) providing a non-contact occupancy sensor to receive an availability indicator from an intended user within the plurality of potential users and transmitting the availability indicator to the CPU, wherein the non-contact occupancy sensor is a proximity sensor mounted to a surgical scrub sink thereby receiving the availability indicator from the intended user when the intended user is positioned within a predetermined range of the non-contact occupancy sensor;
   c) loading medical information into said memory for instruction;
   d) assigning said medical information to at least one of said plurality of potential users;
   e) accessing said medical information assigned to the intended user; and
   f) displaying said assigned medical information to the intended user while the non-contact occupancy sensor senses the presence of the intended user;
   wherein said assigned medical information is medical diagnostic or therapeutic information relating to a medical problem the intended user is currently addressing.

2. The method according to claim 1, wherein the non-contact occupancy sensor includes a voice activation sensor thereby receiving the availability indicator from the intended user when the intended user verbally announces their availability to the voice activation sensor.

3. The method according to claim 1, further comprising a server operably connected to said wireless interactive monitor, wherein said server comprises a plurality of medical accounts assigned to a plurality of medical companies.

4. The method according to claim 3, wherein a medical company uploads medical information to said server according to an assigned medical account.

5. The method according to claim 3, wherein said plurality of medical companies comprise a medical device company or a pharmaceutical company.

6. The method according to claim 3, further comprising updating medical information programming to said wireless interactive monitor from said server on a regular or irregular time interval.

7. The method according to claim 3, further comprising a second wireless interactive monitor, wherein said server selectively communicates with each interactive monitor independently.

8. The method according to claim 1, further including an intended user earpiece that selectively transmits the availability indicator to the non-contact occupancy sensor when the intended user is positioned within a predetermined range of the non-contact occupancy sensor.

\* \* \* \* \*